(12) United States Patent
Hecksher-Sørensen et al.

(10) Patent No.: US 10,610,504 B2
(45) Date of Patent: Apr. 7, 2020

(54) ALPHA-CELL RE-GENERATION COMBINED WITH CONVERSION TO BETA CELLS

(71) Applicants: INSERM (INSTITUT NATIONAL DE LA SANTÉ ET DE LA RECHERCHE MÉDICALE), Paris (FR); CENTRE NATIONAL DE LA RECHERCHE SCIENTIFIQUE, Paris (FR); UNIVERSITE DE NICE SOPHIA ANTIPOLIS-GRAND CHÂTEAU, Nice (FR)

(72) Inventors: Jacob Hecksher-Sørensen, Bagsværd (DK); Patrick Collombat, Nice (FR)

(73) Assignees: INSERM (INSTITUT NATIONAL DE LA SANTÉ ET DE LA RECHERCHE MÉDICALE), Paris (FR); CENTRE NATIONAL DE LA RECHERCHE SCIENTIFIQUE, Paris (FR); UNIVERSITE DE NICE SOPHIA ANTIPOLIS-GRAND CHÂTEAU, Nice (FR)

( * ) Notice: Subject to any disclaimer, the term of this patent is extended or adjusted under 35 U.S.C. 154(b) by 88 days.

(21) Appl. No.: 15/538,031

(22) PCT Filed: Dec. 23, 2015

(86) PCT No.: PCT/EP2015/081141
§ 371 (c)(1),
(2) Date: Jun. 20, 2017

(87) PCT Pub. No.: WO2016/102657
PCT Pub. Date: Jun. 30, 2016

(65) Prior Publication Data
US 2017/0340591 A1    Nov. 30, 2017

(30) Foreign Application Priority Data

Dec. 23, 2014   (EP) .................................. 14199974

(51) Int. Cl.
| | |
|---|---|
| *A61K 39/39* | (2006.01) |
| *A61K 31/197* | (2006.01) |
| *A61K 45/06* | (2006.01) |
| *A61K 35/39* | (2015.01) |
| *C12N 5/071* | (2010.01) |
| *C07K 16/26* | (2006.01) |
| *A61K 39/00* | (2006.01) |
| *A61K 31/00* | (2006.01) |

(52) U.S. Cl.
CPC ............ *A61K 31/197* (2013.01); *A61K 35/39* (2013.01); *A61K 39/00* (2013.01); *A61K 45/06* (2013.01); *C07K 16/26* (2013.01); *C12N 5/0676* (2013.01); *A61K 31/00* (2013.01); *A61K 2039/505* (2013.01); *C07K 2317/76* (2013.01); *C12N 2501/335* (2013.01); *C12N 2501/845* (2013.01); *C12N 2506/22* (2013.01)

(58) Field of Classification Search
CPC ......................... A61K 31/197; A61K 39/3955
See application file for complete search history.

(56) References Cited

U.S. PATENT DOCUMENTS

| 9,463,174 B2 * | 10/2016 | Wang .................. A61K 31/197 |
| 9,708,608 B2 * | 7/2017 | Collombat ........... C12N 5/0676 |
| 2011/0223160 A1 * | 9/2011 | Yan ...................... C07K 14/723 424/133.1 |

* cited by examiner

*Primary Examiner* — Gyan Chandra
(74) *Attorney, Agent, or Firm* — W&C IP (57) ABSTRACT

The present invention relates to methods of generating a population of beta cells from a population of alpha cells, by contacting said population of alpha cells with GABA or a GABA receptor agonist, in combination with a monoclonal glucagon neutralizing antibody or other alpha cell mass regulating compounds, for an improved diabetes therapy.

11 Claims, 5 Drawing Sheets

ALPHA-CELL RE-GENERATION COMBINED WITH CONVERSION TO BETA CELLS

TECHNICAL FIELD

The present invention relates to methods of generating a population of beta cells from a population of alpha cells, by contacting said population of alpha cells with GABA or any GABA receptor agonist with compounds that regulate alpha cell mass by eliminating glucagon signalling such as glucagon neutralizing monoclonal antibody, or such as glucagon receptor antagonists.

BACKGROUND

Diabetes mellitus is characterised by hyperglucagonemia and the failure or loss of the insulin producing beta cells in the pancreas. A way to cure diabetes is therefore to regenerate the functional beta cell mass and/or inhibit glucagon secretion from the alpha cell. Using genetically engineered mouse models, it has been demonstrated that alpha cells can be re-programmed into functional beta cells. Furthermore, the strategy has shown that mice are able to recover several times from a near complete ablation of beta cell mass. This re-programming depends on the interplay between the two transcription factors Arx and Pax4. During development, these were shown to display antagonistic activities in the processes underlying the specification of the endocrine subtype destinies through an inhibitory cross-regulatory circuit that controls the transcriptional state of these two genes (Al-Hasani et al., 2013).

In addition, several studies have demonstrated that GABA participates in maintaining beta-cell mass, by inducing beta-cell proliferation and protecting beta-cells from apoptosis in vitro. It was shown that GABA could decrease blood glucose levels and exert protective and regenerative effects on the beta-cell mass in streptozotocin-induced diabetes in mice. GABA was also found to reverse diabetes in NOD mice (Soltani et al., 2011) and induce proliferation in human islets (Purwana et al., 2014). The suggested explanation was that GABA might act in an autocrine/paracrine manner to regenerate the pancreatic islets via beta-cell proliferation. As described in the patent application WO2014048788 (P. Collombat) 16.09.2013, mice dosed with GABA are able to replenish the beta cell mass by neogenesis and conversion of alpha cells into beta cells.

The absence of glucagon signalling will lead to increased alpha cell mass. This self-renewal process has been shown in several transgenic mouse models: 1) the prohormone convertase-2 knock-out (PC2-KO) that cannot process proglucagon to glucagon (Furuta et al., 1997) and 2) the glucagon-receptor KO (that cannot sense glucagon) both leading to profound alpha-cell hyperplasia (Gelling et al., 2003). Similarly the proglucagon-KO mouse has a vast upregulation of glucagon-negative alpha cells in the islet of Langerhans which express Arx (Hayashi et al., 2009). Moreover, it has been shown that the liver-specific KO of the glucagon receptor has a similar alpha-cell hyperplasia compared to the global glucagon-receptor-KO suggesting the existence of liver derived factors mediating the alpha cell hyperplasia. It has also been shown that alpha cell hyperplasia can be induced in wild type animals. In rabbits immunized with glucagon over 9 months, one notes a dramatic expansion of the alpha cell mass.

Therefore, there is a need for an accelerated mechanism of inducible regeneration of alpha cells with the subsequent conversion into beta cells and reduction of hyperglucagonemia, for optimal therapeutic effect in diabetes patients.

SUMMARY

The present invention provides methods for producing a population of beta cells comprising contacting GABA or a GABA receptor agonist in combination with a glucagon neutralizing monoclonal antibody or other alpha cell mass regulating compounds, in a population of alpha cells.

The present invention further relates to pancreatic beta cells obtainable by the methods of the present invention.

The present invention further relates to the use of GABA or a GABA receptor agonist in combination with a glucagon neutralizing monoclonal antibody or other alpha cell mass regulating compounds to produce a population of beta cells.

The present invention further relates to use of GABA or a GABA receptor agonist in combination with a glucagon neutralizing monoclonal antibody or other alpha cell mass regulating compounds in inter alia in the treatment of glucose intolerance and/or diabetes.

The present invention further relates to a pharmaceutical preparation comprising contacting alpha cells with GABA or a GABA receptor agonist in combination with a glucagon neutralizing monoclonal antibody or other alpha cell mass regulating compounds.

The present invention further relates to a pharmaceutical preparation comprising contacting alpha cells with GABA or a GABA receptor agonist in combination with a glucagon neutralizing monoclonal antibody or other alpha cell mass regulating compounds for use in a method for preventing or treating diabetes.

The present invention further relates to a method for increasing beta cells mass in a patient in need thereof comprising a step of administering in said patient an effective amount of a combination of GABA or a GABA receptor agonist with the monoclonal antibody GLU001 or other alpha cell mass regulating compounds.

The present invention improves the re-generation of alpha cells and subsequent conversion of beta cells, as novel therapy for diabetes.

The present invention aims to improve the beta-like cell neo-genesis mediated by GABA, by combining neutralizing anti-bodies against glucagon and GABA, which increases the alpha-cell mass and increases the cells that can be turned into beta cells.

In one embodiment, the present invention provides an accelerated beta-cell neogenesis by increasing the alpha-cell mass with glucagon neutralizing antibody and GABA by turning induced alpha-cell hyperplasia into a beta-cell hyperplasia.

The invention may also solve further problems that will be apparent from the disclosure of the exemplary embodiments.

DESCRIPTION

The present invention provides methods for producing a population of pancreatic beta cells comprising contacting GABA or a GABA receptor agonist in combination with a glucagon neutralizing monoclonal antibody or other alpha cell mass regulating compounds, in a population of alpha cells.

In one embodiment, the alpha cell mass regulating compounds of the present invention are liver derived factors.

In one embodiment, the alpha cell mass regulating compounds of the present invention are glucagon receptor antagonists.

In one embodiment, the alpha cell mass regulating compounds of the present invention are glucagon receptor signalling inhibitors.

In one embodiment, the present invention relates to pancreatic beta cells obtainable by the methods of the present invention.

In one embodiment, the present invention relates to medical use of GABA or a GABA receptor agonist in combination with a glucagon neutralizing monoclonal antibody or other alpha cell mass regulating compounds in inter alia in the prevention or treatment of diabetes.

In one embodiment, the present invention relates to the use of GABA or a GABA receptor agonist in combination with a glucagon neutralizing monoclonal antibody or other alpha cell mass regulating compounds to produce a population of beta cells.

In one embodiment, the present invention relates to a pharmaceutical preparation comprising contacting alpha cells with GABA or a GABA receptor agonist in combination with a glucagon neutralizing monoclonal antibody or other alpha cell mass regulating compounds.

In one embodiment, the present invention further relates to a method for increasing beta cells mass in a patient in need thereof comprising a step of administering in said patient an effective amount of a combination of GABA or a GABA receptor agonist with the monoclonal antibody GLU001 or other alpha cell mass regulating compounds.

In one embodiment, the present invention improves the re-generation of alpha cells and subsequent conversion of beta cells, as novel therapy for diabetes.

In one embodiment, the present invention aims to improve the beta-like cell neogenesis mediated by GABA, by combining glucagon neutralizing antibodies with GABA, which increases the alpha-cell mass and increases the cells that can be turned into beta cells.

In one embodiment, the present invention provides an accelerated beta-cell neogenesis by increasing the alpha-cell mass with glucagon neutralizing antibody and GABA by turning induced alpha-cell hyperplasia into new beta-cells.

In one embodiment, the present invention aims to improve blood glucose by decreasing glucagon signalling.

The term "diabetes" or "diabetes mellitus" includes type 1 diabetes, type 2 diabetes, gestational diabetes (during pregnancy) and other states that cause hyperglycaemia. The term is used for a metabolic disorder in which the pancreas produces insufficient amounts of insulin, or in which the cells of the body fail to respond appropriately to insulin thus preventing cells from absorbing glucose. As a result, glucose builds up in the blood.

Type 1 diabetes, also called insulin-dependent diabetes mellitus (IDDM) and juvenile-onset diabetes, is caused by beta-cell destruction, usually leading to absolute insulin deficiency.

Type 2 diabetes, also known as non-insulin-dependent diabetes mellitus (NIDDM) and adult-onset diabetes, is associated with predominant insulin resistance and thus relative insulin deficiency and/or a predominantly insulin secretory defect with insulin resistance.

The term "treatment" is meant to include both the prevention and minimization of the referenced disease, disorder, or condition (i.e., "treatment") refers to both prophylactic and therapeutic administration of GABA and Glu001 or composition comprising GABA and Glu001 unless otherwise indicated or clearly contradicted by context.

The route of administration may be any route which effectively transports a compound of this invention to the desired or appropriate place in the body, such as parenterally, for example, subcutaneously, intramuscularly or intravenously. Alternatively, a compound of this invention can be administered orally, pulmonary, rectally, transdermally, buccally, sublingually, or nasally.

The amount of a compound of this invention to be administered, the determination of how frequently to administer a compound of this invention, and the election of which compound or compounds of this invention to administer, optionally together with another antidiabetic compound, is decided in consultation with a practitioner who is familiar with the treatment of diabetes.

As used herein, the term "pancreatic beta-cells", "beta-cells" or "insulin-secreting beta cells" are used interchangeably and refer to cells capable of producing insulin upon stimulation with glucose. More preferably, the expression of specific surface antigens is used to determine whether a cell is a pancreatic beta-cell. For instance, pancreatic beta-cells express the glucose transporter, Glut2. Alternatively, the expression of specific transcription factors is used to determine whether a cell is a pancreatic beta-cell. For instance, pancreatic beta-cells highly express the transcription factors Pdx1, Nkx6.1, MafA and Pax4.

As used herein, the terms "pancreatic alpha-cells", "alpha-cells" or "glucagon-expressing cells" are used interchangeably and refer to cells capable of expressing glucagon as a consequence of decreased blood sugar levels. More preferably, the expression of specific transcription factors is used to determine whether a cell is a pancreatic alpha-cell. For instance, pancreatic alpha-cells express the transcription factors Arx, Brn-4 and MafB.

As used herein, the term "receptor agonist" refers to the native ligand of that receptor (e.g., a GABA receptor) to analogues thereof or other ligands that similarly" activate" the receptor, and/or to a positive allosteric modulator of the receptor.

As used herein, the term "GABA" refers to gamma-amino butyric acid of formula (1) or a pharmaceutically acceptable salt, solvate or prodrug thereof as well as mixtures thereof:

As used herein, the term "$GABA_A$ receptor specific agonist" refers to an agent that has agonistic activity at the $GABA_A$ receptor and substantially no agonist activity at the $GABA_B$.

As used herein, "$GABA_A$ receptor preferential agonist" refers to an agent that has greater agonistic activity at the $GABA_A$ receptor than at the $GABA_B$. Typically, the $GABA_A$ receptor preferential agonist has at least 1.2-fold, more preferably at least 1.5 fold still more preferably at least 2 fold, and most preferably at least 3-fold, at least 5-fold, or at least 10-fold greater activity at the $GABA_A$ receptor than at the $GABA_B$ and as determined using an conventional assay for agonist activity at a GABA receptor.

As used herein, the term "$GABA_B$ receptor specific agonist" refers to an agent that has agonistic activity at the $GABA_B$ receptor and substantially no agonist activity at the $GABA_A$.

As used herein, "$GABA_B$ receptor preferential agonist" refers to an agent that has greater agonistic activity at the $GABA_B$ receptor than at the $GABA_A$. In certain embodiments the GABAB receptor preferential agonist has at least 1.2-fold, more preferably at least 1.5 fold still more preferably at least 2 fold, and most preferably at least 3-fold, at least 5-fold, or at least 10-fold greater activity at the $GABA_B$ receptor than at the $GABA_A$ as determined using an conventional assay for agonist activity at a GABA receptor.

In one particular embodiment the GABA receptor agonist acts on both GABA-A and GABA-B receptors. In one particular embodiment, the GABA receptor agonist acts preferentially, or exclusively, on the GABAA or GABAB receptor.

GABA receptor agonists are well known to those of skill in the art.

Non-limiting examples of GABA receptor agonists include: certain barbiturates (e.g., thiopental, thiamylal, pentobarbital, secobarbital, hexobarbital, butobarbital, amobarbital, barbital, mephobarbital, phenobarbital, primidone, and the like), certain benzodiazepines (e.g., midazolam, triazolam, lometazepam, flutazolam, nitrazepam, fluritrazepam, nimetazepam, diazepam, medazepam, oxazolam, prazeam, tofisopam, rilmazafonoe, lorazepam, temazepam, oxazepam, fluidazepam, cWordizaepoxide, cloxazolam, flutoprazepam, alprazolam, estazolam, bromazepam, flurazepam, clorazepate potassium, haloxazolam, ethylloflazepate, qazepam, clonazepam, mexazolam, and the like), certain thienodiazepiens (e.g., etizolam, brotizolam, clotizaepam, and the like), certain dialkylphenols (e.g., propofol, fospropofol, and the like), certain non-benzodiazepines (e.g., Zolpidem, zopiclone, exzopiclone, etc.), and the like.

In another embodiment, the GABA receptor agonist is selected from the group consisting of muscimol, THIP/gaboxadol, isoguvacine, kojic amine, homotaurine, homohypotaurine, trans-aminocyclopentane-3-carboxylic acid, trans-amino-4-crotonic acid, p-guanidinopropionic acid, homo-P-proline, isonipecotic acid, 3-((aminoiminomethyl)thio)-2-propenoic acid (ZAPA), imidazoleacetic acid, and piperidine-4-sulfonic acid (P4S). Alternatively, glutamate decarboxylase or glutamic acid decarboxylase (GAD) which is enzymes that catalyzes the decarboxylation of glutamate to GABA and CO2 may be used.

As used herein, the term "alpha cell mass regulating compounds" refers to compounds that mimic the neutralisation of functional glucagon receptor (GluR) signalling which in mouse and man is known to vastly upregulate alpha cell mass. The list of alpha cell mass regulating compounds includes but is not limited to all molecules and biologics that will 1) prevent glucagon from binding and activating its receptor 2) prevent the production or processing of glucagon 3) prevent the production or downstream signalling from the glucagon receptor 4) secreted liver-derived factors produced in response to absence of glucagon signalling.

As used herein, the term "glucagon" refers to the the proglucagon derived peptide sequence which is 100% conserved between mouse and man. Glucagon is well known to increase blood glucose through activation of the glucagon-receptor (GluR) in the liver. Absence in GluR signalling leads to lowering of blood-glucose and alpha-cell hyperplasia.

As used herein, the term "glucagon neutralising monoclonal antibody" refers to an antibody that will prevent glucagon from binding and activating the glucagon receptor (GluR). In one embodiment, "glucagon neutralising monoclonal antibody" refers to an antibody that has strong binding affinity to glucagon, thereby preventing glucagon from binding and activating the glucagon receptor (GluR).

In another embodiment, "glucagon neutralising monoclonal antibody" refers to an antibody that will bind to the glucagon receptor, thereby preventing glucagon from binding and activating the glucagon receptor (GluR).

Non-limiting examples of "glucagon neutralizing" antibodies including but not limited to monoclonal antiglucagon antibodies such as, but not limited to, Glu-mAb (NovoClone GLU-001, Novo Nordisk, Bagsvaerd, Denmark), or aGCGR (antibody sharing VH and VL domains with Amgen A-3 as disclosed in US 2011/0223160). or similar (including but not limited to a "humanized version of GLU001"). As used herein, the "GLU001, Glu001, GLU-001 or Glu-001" refers to a mouse monoclonal antibody which binds mammalian glucagon (mouse and human glucagon is identical). Glu001 is a class IgG 1 antibody produced by a hybridoma selected from a fusion of BALB/c spleen cells and X63-AG8-6.5,3 myeloma cells. By a competitive radioimmunoassay method the association constant (Ka) was determined to 0.6.10¹~1/mol. Total binding capacity of Glu-001, as calculated from Scatchard analysis, was 40 nmol/ml. Binding studies with synthetic glucagon fragments indicated that the antibody-binding epitope was localized to segment 5-15 of the amino acid sequence of glucagon. The cross-reactivity against glicentin (a glucagon-containing fragment of proglucagon) was determined to be 100%. There was no binding to glucagon-like peptide 1, gastric inhibitory polypeptide, glicentin-related pancreatic peptide, vasoactive intestinal polypeptide or pancreatic polypeptide. Glu-001 was produced in cell-culture and purified and concentrated on a protein-A Sepharose column (Brand et al., 1994).

Screening approach for antagonistic antibodies that prevent glucagon binding to glucagon receptor include two different assays described below. Common for the two assays is that an antibody with similar properties as GLU001 or aGCGR is able to prevent glucagon induced signalling and binding.

Assay A: Displacement Assay: Flow Cytometry
Assay Principle

In order to determine the ability of test antibodies to antagonize binding of glucagon to its receptor a displacement assay using flow cytometry is applied. Selected glucagon or glucagon receptor specific antibodies are tested for the ability to block the FLAG or biotinylated tagged glucagon binding to the receptor transfected cells. As a control non-transfected cells and irrelevant antibodies are used.

Assay Protocol

The assay is performed by adding 50 µl/well of diluted monoclonal antibodies in titration (5 ug/ml, 2.5 ug/ml, 1.25 ug/ml, 0.63 ug/ml, 0.31 ug/ml, 0.16 ug/ml, 0.08 and 0 ug/ml tested in duplicates) to the receptor positive cells (50000 cells pr well) and incubated at 4° C. for 1 hour in the presence of FLAG or biotinylated tagged glucagon at a fixed concentration (one series at 20 ng/ml and one series at 2 ng/ml) in a 96 well plate (Greiner, cat no. 65021). After incubation and wash (PBS buffer with 5% Fetal Bovine serum (FBS), centrifuge for 5 minutes at 200 g) 50 ul/well secondary antibody (APC anti-FLAG tag ab from Perkin Elmer in a Final conc. of 5 µg/ml) or streptavidin-APC (diluted in PBS buffer 1:400) is added and incubated for another 1 hour at 4° C. Cells are washed and fixed by paraformaldehyde (1% weight in volume (w/v) paraformaldehyde). Samples are analysed using eg. BD FACS Canto flow cytometer. Signals were collected in the APC-channel. Analysis of results was done using GraphPad Prism Software (version 5).

Assay B: Reporter Gene Assay
Assay Principle

In order to determine the ability of test antibodies to antagonize glucagon for activation of its receptor a reporter gene assay using flow cytometry is applied. Selected glucagon or glucagon receptor specific antibodies are tested for the ability to prevent activation of the glucagon receptor. As a control non-transfected cells and irrelevant antibodies are used. The cell line used is BHK overexpressing the glucagon receptor and luciferase under the control of a cAMP inducible promotor (CRE). Cells are cultivated in a 96 well plate overnight and subsequently stimulated with glucagon in the presence or absence of antibody for 3 hours. When the cells, which express the functional glucagon receptor, are stimulated with glucagon, a rise in intracellular cAMP occurs. This causes the cells to produce luciferase. The activity of luciferase is measured in lysed cells by adding luciferin (Steady Glo). Luciferin is turned into oxiluciferin by the equation shown below. Luminescencen is measured by a eg. Envision (Perkin Elmer).

Assay Protocol

The cells, BHK h-GlucagonR+luc pLj6-4-25, are grown overnight in 96-well plates with 75.000 c/well in 100 ul DMEM with 10% FBS at 37° C. and 5% $CO_2$. Medium is replaced with 100 ul/well assay medium (DMEM containing 10% FBS) containing glucagon (one series at 20 ng/ml and one series at 2 ng/ml) and titrated levels of relevant antibody (5 ug/ml, 2.5 ug/ml, 1.25 ug/ml, 0.63 ug/ml, 0.31 ug/ml, 0.16 ug/ml, 0.08 and 0 ug/ml tested in duplicates) is added. Plates are incubated in the incubator for three hours. The plates are incubated at room temperature for 15 min. 50 ul/well Steady Glo (Promega) is added. After 20-30 min the plates are read by eg. Envision reader.

Antibodies that bind to the same antigen can be characterised with respect to their ability to bind to their common antigen simultaneously and may be subjected to "competition binding"/"binning". In the present context, the term "binning" refers to a method of grouping antibodies that bind to the same antigen. "Binning" of antibodies may be based on competition binding of two antibodies to their common antigen in assays based on standard techniques such as surface Plasmon resonance (SPR), ELISA or flow cytometry.

An antibody's "bin" is defined using a reference antibody. If a second antibody is unable to bind to an antigen at the same time as the reference antibody, the second antibody is said to belong to the same "bin" as the reference antibody. In this case, the reference and the second antibody competitively bind the same part of an antigen and are coined "competing antibodies". If a second antibody is capable of binding to an antigen at the same time as the reference antibody, the second antibody is said to belong to a separate "bin". In this case, the reference and the second antibody do not competitively bind the same part of an antigen and are coined "non-competing antibodies".

Non-limiting examples of "siRNA targeting the glucagon receptor" include short interfering oligonucleotides sequences that will promote removal or degradation of the glucagon receptor mRNA. Such molecules have been described for treatment of type 2 diabetes.

The term "ligand" herein refers to any substance that is able to bind to and form a complex with a biomolecule, in order to serve a biological purpose. In one sense of the term, it is a signal triggering molecule binding to a site on a target protein by means of intermolecular forces such as ionic bonds, hydrogen bonds and Van der Waals. The association of a ligand with said biomolecule is usually reversible. Binding of a naturally occurring ligand to its counterpart receptor may or may not alter the conformation of the receptor protein.

The ligand component of the proteins of the current invention may be an antibody or a fragment thereof.

The term "antibody" herein refers to a protein, derived from a germline immunoglobulin sequence, which is capable of specifically binding to an antigen or a portion thereof. The term antibody includes full length antibodies of any class (or isotype), that is, IgA, IgD, IgE, IgG, IgM and/or IgY. An antibody that specifically binds to an antigen, or portion thereof, may bind exclusively to that antigen, or portion thereof, or it may bind to a limited number of homologous antigens, or portions thereof.

Natural full-length antibodies usually comprise at least four polypeptide chains: two heavy (H) chains and two light (L) chains that are connected by disulfide bonds. In some cases, natural antibodies comprise less than four chains, as in the case of the heavy chain only antibodies found in camelids ($V_HH$ fragments) and the IgNARs found in Chondrichthyes. One class of immunoglobulins of particular pharmaceutical interest are the IgGs. In humans, the IgG class may be sub-divided into 4 sub-classes IgG1, IgG2, IgG3 and IgG4, based on the sequence of their heavy chain constant regions. The light chains can be divided into two types, kappa and lambda chains based on differences in their sequence composition. IgG molecules are composed of two heavy chains, interlinked by two or more disulfide bonds, and two light chains, each attached to a heavy chain by a disulfide bond. An IgG heavy chain may comprise a heavy chain variable region (VH) and up to three heavy chain constant (CH) regions: CH1, CH2 and CH3. A light chain may comprise a light chain variable region (VL) and a light chain constant region (CL). VH and VL regions can be further subdivided into regions of hypervariability, termed complementarity determining regions (CDRs) or hypervariable regions (HvRs), interspersed with regions that are more conserved, termed framework regions (FR). VH and VL regions are typically composed of three CDRs and four FRs, arranged from amino-terminus to carboxy-terminus in the following order: FR1, CDR1, FR2, CDR2, FR3, CDR3, FR4. The variable domains with the hypervariable regions of the heavy and light chains form a binding domain that is capable of interacting with an antigen, whilst the constant region of an antibody may mediate binding of the immunoglobulin to host tissues or factors, including, but not limited to various cells of the immune system (effector cells), Fc receptors and the first component (C1q) of the C1 complex of the classical complement system.

Antibodies of the invention may be monoclonal antibodies, in the sense that they represent a set of unique heavy and light chain variable domain sequences as expressed from a single B-cell or by a clonal population of B cells. Antibodies of the invention may be produced and purified using various methods that are known to the person skilled in the art. For example, antibodies may be produced from hybridoma cells. Antibodies may be produced by B-cell expansion. Antibodies or fragments thereof may be recombinantly expressed in mammalian or microbial expression systems, or by in-vitro translation. Antibodies or fragments thereof may also be recombinantly expressed as cell surface bound molecules, by means of e.g. phage display, bacterial display, yeast display, mammalian cell display or ribosome or mRNA display. Once produced, antibodies may be screened for binding to glucagon.

Antibodies of the current invention may be isolated. The term "isolated antibody" refers to an antibody that has been separated and/or recovered from (an) other component(s) in the environment in which it was produced and/or that has been purified from a mixture of components present in the environment in which it was produced.

Certain antigen-binding fragments of antibodies may be suitable in the context of the current invention, as it has been shown that the antigen-binding function of an antibody can be performed by fragments of a full-length antibody. The term "antigen-binding fragment" of an antibody refers to one or more fragment(s) of an antibody that retain the ability to specifically bind to an antigen, such as glucagon or another target molecule, as described herein. Examples of antigen-binding fragments include Fab, Fab', F(ab)2, F(ab')2, F(ab)S, Fv (typically the VL and VH domains of a single arm of an antibody), single-chain Fv (scFv; see e.g. Bird et al., Science 1988; 242:42S-426; and Huston et al. PNAS 1988; 85:5879-5883), dsFv, Fd (typically the VH and CHI domain), and dAb (typically a VH domain) fragments; VH, VL, VhH, and V-NAR domains; monovalent molecules comprising a single VH and a single VL chain; minibodies, diabodies, triabodies, tetrabodies, and kappa bodies (see, e.g., Ill et al. Protein Eng 1997; 10:949-57); camel IgG; IgNAR; as well as one or more isolated CDRs or a functional paratope, where the isolated CDRs or antigen-binding residues or polypeptides can be associated or linked together so as to form a functional antibody fragment.

Various types of antibody fragments have been described or reviewed in, e.g., Holliger and Hudson, Nat Biotechnol 2005; 25:1126-1136; WO2005040219, and published U.S. Patent Applications 20050238646 and 20020161201. These antibody fragments may be obtained using conventional techniques known to those of skill in the art, and the fragments may be screened for utility in the same manner as intact antibodies.

"Fab fragments" of an antibody, including "Fab" and "F(ab')$_2$" fragments, are derived from said antibody by cleavage of the heavy chain in the hinge region on the N-terminal or C-terminal side of the hinge cysteine residues connecting the heavy chains of the antibody. A "Fab" fragment includes the variable and constant domains of the light chain and the variable domain and the first constant domain (CH1) of the heavy chain. "F(ab')$_2$" fragments comprise a pair of "Fab'" fragments that are generally covalently linked by their hinge cysteines. A Fab' is formally derived from a F(ab')$_2$ fragment by cleavage of the hinge disulfide bonds connecting the heavy chains in the F(ab')$_2$. Other chemical couplings than disulfide linkages of antibody fragments are also known in the art. A Fab fragment retains the ability of the parent antibody to bind to its antigen, potentially with a lower affinity. F(ab')$_2$ fragments are capable of divalent binding, whereas Fab and Fab' fragments can bind monovalently. Generally, Fab fragments lack the constant CH2 and CH3 domains, i.e. the Fc part, where interaction with the Fc receptors would occur. Thus, Fab fragments are in general devoid of effector functions. Fab fragments may be produced by methods known in the art, either by enzymatic cleavage of an antibody, e.g. using papain to obtain the Fab or pepsin to obtain the F(ab')$_2$, Fab fragments including Fab, Fab', F(ab')$_2$ may be produced recombinantly using techniques that are well known to the person skilled in the art.

An "Fv" fragment is an antibody fragment that contains a complete antigen recognition and binding site, and generally comprises a dimer of one heavy and one light chain variable domain in association that can be covalent in nature, for example in a single chain variable domain fragment (scFv). It is in this configuration that the three hypervariable regions of each variable domain interact to define an antigen-binding site on the surface of the VH-VL dimer. Collectively, the six hypervariable regions or a subset thereof confer antigen binding specificity to the antibody. However, even a single variable domain comprising only three hypervariable regions specific for an antigen can retain the ability to recognize and bind antigen, although usually at a lower affinity than the entire binding site (Cai & Garen, *Proc. Natl. Acad. Sci. USA,* 93: 6280-6285, 1996). For example, naturally occurring camelid antibodies that only have a heavy chain variable domain (VHH) can bind antigen (Desmyter et al., *J. Biol. Chem.,* 277: 23645-23650, 2002; Bond et al., *J. Mol. Biol.* 2003; 332: 643-655).

"Single-chain Fv" or "scFv" antibody fragments comprise the VH and VL domains of antibody, where these domains are present in a single polypeptide chain. Generally, the Fv polypeptide further comprises a polypeptide linker between the VH and VL domains that enables the scFv to form the desired structure for antigen binding. For a review of scFv, see Pluckthun, 1994, In: The Pharmacology of Monoclonal Antibodies, Vol. 113, Rosenburg and Moore eds. Springer-Verlag, New York, pp. 269-315.

The term "diabodies" refers to small antibody fragments with two antigen-binding sites, in which fragments comprise a heavy chain variable domain (VH) connected to a light chain variable domain (VL) in the same polypeptide chain (VH and VL). By using a linker that is too short to allow pairing between the two variable domains on the same chain, the variable domains are forced to pair with complementary domains of another chain, creating two antigen-binding sites. Diabodies are described more fully, for example, in EP 404,097; WO 93/11161; and Hollinger et al., 1993, *Proc. Natl. Acad. Sci. USA*, 90:6444-6448.

The expression "linear antibodies" refers to antibodies as described in Zapata et al., 1995, *Protein Eng.*, 8(10):1057-1062. Briefly, these antibodies contain a pair of tandem Fd segments (VH-CH1-VH-CH1) that, together with complementary light chain polypeptides, form a pair of antigen binding regions. Linear antibodies can be bispecific or monospecific.

The term "monobody" as used herein, refers to an antigen binding molecule with a heavy chain variable domain and no light chain variable domain. A monobody can bind to an antigen in the absence of light chains and typically has three hypervariable regions, for example CDRs designated CDRH1, CDRH2, and CDRH3. A heavy chain IgG monobody has two heavy chain antigen binding molecules connected by a disulfide bond. The heavy chain variable domain comprises one or more hypervariable regions, preferably a CDRH3 or HVL-H3 region.

Antibody fragments may be obtained using conventional recombinant or protein engineering techniques and the fragments can be screened for binding to glucagon, or another function, in the same manner as intact antibodies.

Antibody fragments of the invention may be made by truncation, e.g. by removal of one or more amino acids from the N and/or C-terminal ends of a polypeptide. Fragments may also be generated by one or more internal deletions.

An antibody of the invention may be, or may comprise, a fragment of the Glu001 antibody, the Glu001 antibody or a variant of any one of these antibodies. An antibody of the invention may be, or may comprise, an antigen binding portion of one of these antibodies, or variants thereof. For example, the antibody of the invention may be a Fab fragment of one of these antibodies or variants thereof, or it may be a single chain antibody derived from one of these antibodies, or a variant thereof.

An antibody of the invention may be a human antibody or a humanised antibody. The term "human antibody", as used herein, is intended to include antibodies having variable regions in which at least a portion of a framework region and/or at least a portion of a CDR region are derived from human germline immunoglobulin sequences. (For example, a human antibody may have variable regions in which both the framework and CDR regions are derived from human germline immunoglobulin sequences.) Furthermore, if the antibody contains a constant region, the constant region is also derived from human germline immunoglobulin sequences. The human antibodies of the invention may include amino acid residues not encoded by human germline immunoglobulin sequences (e.g., mutations introduced by random or site-specific mutagenesis in vitro or by somatic mutation in vivo).

Such a human antibody may be a human monoclonal antibody. Such a human monoclonal antibody may be produced by a hybridoma which includes a B cell obtained from a transgenic nonhuman animal, e.g., a transgenic mouse, having a genome comprising human immunoglobulin heavy and light chain gene segments repertoires, fused to an immortalized cell.

Human antibodies may be isolated from sequence libraries built on selections of human germline sequences, further diversified with natural and synthetic sequence diversity.

Human antibodies may be prepared by in vitro immunisation of human lymphocytes followed by transformation of the lymphocytes with Epstein-Barr virus.

The term "human antibody derivative" refers to any modified form of the human antibody, such as a conjugate of the antibody and another agent or antibody.

The term "humanised antibody", as used herein, refers to a human/non-human chimeric antibody that contains a sequence (CDR regions or parts thereof) derived from a non-human immunoglobulin. A humanised antibody is, thus, a human immunoglobulin (recipient antibody) in which at least residues from a hyper-variable region of the recipient are replaced by residues from a hyper-variable region of an antibody from a non-human species (donor antibody) such as from a mouse, rat, rabbit or non-human primate, which have the desired specificity, affinity, sequence composition and functionality. In some instances, FR residues of the human immunoglobulin are replaced by corresponding non-human residues. An example of such a modification is the introduction of one or more so-called back-mutations, which are typically amino acid residues derived from the donor antibody. Humanisation of an antibody may be carried out using recombinant techniques known to the person skilled in the art (see, e.g., Antibody Engineering, Methods in Molecular Biology, vol. 248, edited by Benny K. C. Lo). A suitable human recipient framework for both the light and heavy chain variable domain may be identified by, for example, sequence or structural homology. Alternatively, fixed recipient frameworks may be used, e.g., based on knowledge of structure, biophysical and biochemical properties. The recipient frameworks can be germline derived or derived from a mature antibody sequence. CDR regions from the donor antibody can be transferred by CDR grafting. The CDR grafted humanised antibody can be further optimised for e.g. affinity, functionality and biophysical properties by identification of critical framework positions where re-introdution (backmutation) of the amino acid residue from the donor antibody has beneficial impact on the properties of the humanised antibody. In addition to donor antibody derived backmutations, the humanised antibody can be engineered by introduction of germline residues in the CDR or framework regions, elimination of immunogenic epitopes, site-directed mutagenesis, affinity maturation, etc.

Furthermore, humanised antibodies may comprise residues that are not found in the recipient antibody or in the donor antibody. These modifications are made to further refine antibody performance. In general, a humanised antibody will comprise at least one—typically two—variable domains, in which all or substantially all of the CDR regions correspond to those of a non-human immunoglobulin and in which all or substantially all of the FR residues are those of a human immunoglobulin sequence. The humanised antibody can, optionally, also comprise at least a portion of an immunoglobulin constant region (Fc), typically that of a human immunoglobulin.

The term "humanised antibody derivative" refers to any modified form of the humanised antibody, such as a conjugate of the antibody and another agent or antibody.

The term "chimeric antibody", as used herein, refers to an antibody whose light and heavy chain genes have been constructed, typically by genetic engineering, from immunoglobulin variable and constant region genes that originate from different species. For example, the variable segments of genes from a mouse monoclonal antibody may be joined to human constant regions.

The term "antigen" (Ag) refers to the molecular entity used for immunisation of an immunocompetent vertebrate to produce the antibody (Ab) that recognizes the Ag. Herein, Ag is termed more broadly and is generally intended to include target molecules that are specifically recognized by the Ab, thus including fragments or mimics of the molecule used in the immunisation process, or other process, e.g. phage display, used for generating the Ab.

The term "epitope", as used herein, is defined in the context of a molecular interaction between an "antigen binding polypeptide", such as an antibody (Ab), and its corresponding antigen (Ag). Generally, "epitope" refers to the area or region on an Ag to which an Ab specifically binds, i.e. the area or region in physical contact with the Ab. Physical contact may be defined using various criteria (e.g. a distance cut-off of 2-6 Å, such as 3 Å, such as 4 Å, such as 5 Å; or solvent accessibility) for atoms in the Ab and Ag molecules. A protein epitope may comprise amino acid residues in the Ag that are directly involved in binding to a Ab (also called the immunodominant component of the epitope) and other amino acid residues, which are not directly involved in binding, such as amino acid residues of the Ag which are effectively blocked by the Ab, i.e. amino acid residues within the "solvent-excluded surface" and/or the "footprint" of the Ab.

The term epitope herein comprises both types of binding region in any particular region of glucagon that specifically binds to an anti-glucagon antibody, or another glucagon-specific agent according to the invention, unless otherwise stated. Glucagon may comprise a number of different epitopes, which may include, without limitation, (1) linear peptide epitopes (2) conformational epitopes which consist of one or more non-contiguous amino acids located near each other in the mature glucagon conformation; and (3) post-translational epitopes which consist, either in whole or part, of molecular structures covalently attached to glucagon such as carbohydrate groups.

The epitope for a given antibody (Ab)/antigen (Ag) pair can be described and characterized at different levels of detail using a variety of experimental and computational epitope mapping methods. The experimental methods include mutagenesis, X-ray crystallography, Nuclear Magnetic Resonance (NMR) spectroscopy, Hydrogen deuterium eXchange Mass Spectrometry (HX-MS) and various competition binding methods; methods that are known in the art. As each method relies on a unique principle, the description of an epitope is intimately linked to the method by which it has been determined. Thus, depending on the epitope mapping method employed, the epitope for a given Ab/Ag pair may be described differently. At its most detailed level, the epitope for the interaction between the Ag and the Ab can be described by the spatial coordinates defining the atomic contacts present in the Ag-Ab interaction, as well as information about their relative contributions to the binding thermodynamics. At a less detailed level, the epitope can be characterized by the spatial coordinates defining the atomic contacts between the Ag and Ab. At an even less detailed level the epitope can be characterized by the amino acid residues that it comprises as defined by a specific criteria such as the distance between or solvent accessibility of atoms in the Ab:Ag complex. At a further less detailed level the epitope can be characterized through function, e.g. by competition binding with other Abs. The epitope can also be defined more generically as comprising amino acid residues for which substitution by another amino acid will alter the characteristics of the interaction between the Ab and Ag.

From the fact that descriptions and definitions of epitopes, dependant on the epitope mapping method used, are obtained at different levels of detail, it follows that comparison of epitopes for different Abs on the same Ag can similarly be conducted at different levels of detail.

In one embodiment, GLU001 is co-formulated with GABA to obtain maximal regeneration of functional beta cell mass.

In a further embodiment, other compounds that prevent GluR signaling (e.g. glucagon receptor antagonists, inhibitory siRNA targeting the glucagon receptor) that stimulate alpha cell mass increase will be co-formulated with GABA receptor agonists.

In one embodiment the present invention provides an accelerated restoration of functional beta cell mass method compared to that known in the art for alpha-cell regeneration and subsequent beta cell conversion.

In one embodiment, the present invention provides a desired reduction in glucagon levels.

In one embodiment, the present invention provides sufficient endogenous insulin production by genuine pancreatic beta cells.

In one embodiment, the present invention provides a faster alpha-cell regeneration. A faster alpha-cell regeneration and thereby the possibility of a faster beta-like cell neogenesis to beta cells, is desirable to speed up return to normal glycaemia and thereby reduce side effects and complications. A faster alpha-cell regeneration is also relevant for a potential cure for diabetes.

The elimination of glucagon signalling enhances the production of new alpha cells. When combining the GABA-receptor agonist mediated alpha to beta cell conversion with the impaired glucagon signalling the beta-cell regeneration is greatly augmented. The combined principle of alpha to beta cell conversion (GABA-receptor agonist) with more efficient alpha cell replenishment (through elimination of glucagon signalling) provides a powerful and more efficient therapy of diabetes.

Surprisingly, the combination of GABA and GLU001 allows for a significant improvement of beta-like cell neogenesis and a much desired reduction in glucagon levels. Indeed, GLU001 promotes efficient glucagon-depletion and increased alpha-cell mass, such hyperplastic alpha-cells being turned into beta-like cells upon GABA administration. Thus, beta-like cell neogenesis is dramatically faster using this combination as compared to the sole administration of GABA and is therefore of great interest in the context of diabetes therapy.

Embodiments

1. A method for producing a population of pancreatic beta cells comprising the step of contacting a population of alpha cells with GABA or a GABA receptor agonist in combination with a glucagon neutralizing monoclonal antibody or other alpha cell mass regulating compounds.

2. The method of embodiment 1, wherein the glucagon neutralizing monoclonal antibody binds to glucagon.

3. The method of embodiment 1, wherein said glucagon neutralizing monoclonal antibody is GLU001.

4. The method of embodiment 1, wherein glucagon neutralizing monoclonal antibody competes with GLU001 for binding to glucagon.

5. The method of embodiment 1, wherein glucagon neutralizing monoclonal antibody binds to same epitope as GLU001.

6. The method of embodiment 1, wherein said alpha cell mass regulating compounds are secreted factors, such as factors derived from the liver.

7. The method of embodiment 1, wherein said alpha cell mass regulating compounds are glucagon receptor antagonists.

8. A pharmaceutical preparation (combination or pharmaceutical composition or a kit-of-part) comprising GABA or a GABA receptor agonist in combination with the monoclonal antibody GLU001 or other alpha cell mass regulating compounds.

9. A pharmaceutical preparation according to embodiment 8, for use in treatment of diabetes.

10. Use of GABA or a GABA receptor agonist in combination with a glucagon neutralising monoclonal antibody, to produce a population of pancreatic beta cells.

11. Use of embodiment 10, wherein the neutralising monoclonal antibody is Glu001.

12. A method for increasing beta cells mass in a patient in need thereof comprising a step of administering in said patient an effective amount of a combination of GABA or a GABA receptor agonist with the monoclonal antibody GLU001 or other alpha cell mass regulating compounds.

EXAMPLES

List of Abbreviations
Arx: aristaless related homeobox gene
BrdU: Bromodeoxyuridine
GABA: gamma-Aminobutyric acid
GluR:Glucagon receptor
Pax4: Paired box gene 4
siRNA: short interfering RNA
Pdx1: Pancreatic and duodenal homeobox 1
MafA: Transcription factor MafA
Nkx6.1: NK6 homeobox 1
PC2: Proprotein convertase 2
General Methods All mice were bred and delivered from Taconics (Ry, Denmark). The mice were kept at either at the Animal Unit (Novo Nordisk, Måløv, Denmark) or at the Valrose facility (Nice-FR) during the experiments. Animals were kept and experiments were performed according to Danish law and intern standards of Novo Nordisk A/S or according to French ethical regulations Mouse Lines:

NMRI, C57Bl6 and 129SV mice originally from the Naval Medical Research Institute (NMRI) and The Jackson Laboratory. Mice used for the experiments were 1-48 weeks old.

Blood Glucose Measurements:

The mice were fed ad libitum in all experiments. Blood was collected from the tail tips of the mice into 10 µl glass tubes, transferred to glucose/lactate system solution (EKF-diagnostic, 0201-0002-024) and analysed on BIOSEN S_line (EKF-diagnostic). The BIOSEN S_line device measure glucose concentration by enzymatic amperometric analysis.

Glucagon Dosing:

Glucagon from GlucaGen® HypoKit (Novo Nordisk) was dissolved in sterile $H_2O$ and diluted in sterile 0.9% saline (DAK). The glucagon solution was injected into the tail vene of the mice. A concentration of 2.86 pmol/g bw was used.

Glucagon Measurements:

The mice were fed ad libitum in all experiments. Blood was collected from the sublingual vein and centrifuged to obtain plasma. Glucagon levels were measured using Luminescence Oxygen Channeling Immunoassay (LOCI).

Labelling of Dividing Cells with 5-Bromo-2'-deoxyuridine (BrdU):

BrdU is a synthetic nucleoside analogue of thymidine. BrdU is incorporated when the cells synthesize DNA. Subsequently, BrdU can be detected by an antibody. BrdU (MP Biomedicals, #100171) were administrated to the mice by the drinking water (0.9 mg/ml). The bottles were coved by aluminum foil to protect the BrdU from light. The water was changed twice a week.

Processing of Tissue for Proliferation (IHC):

The mice were killed by cervical dislocation. The pancreas was quickly removed, washed in cold PBS, and fixed in 4% PFA at 4° C. for 8 hours. Subsequently, the pancreas was washed in PBS, incubated in 30% sucrose in PBS overnight, embedded in Tissue-Tek O.C.T Compound (Sakura Finetek) and cut into 10 µm sections on a cryostate. Antigen retrieval was used for detection of KI-67 (citrate buffer pH=6.0, microwave) and BrdU (citrate buffer pH=6.0, microwave and 2M HCl for 30 min). Sections were blocked for at least 1 h in 0.5% TNB blocking buffer (PerkinElmer #NEL704A001KT) before antibodies (diluted in 0.5% TNB blocking buffer) were applied. Sections were incubated with primary antibodies o.n., washed 3 times in PBS, and incubated with secondary antibody for 30 min-1 h. Finally the section were washed 3 times in PBS and mounted in glycerol-based mounting medium (KPL #71-00-16).

Antibodies Used for Proliferation:

Immunohistochemistry exploits the principle of antibodies binding specifically to antigens in biological tissues. By using secondary antibody linked to a fluorophore, the antigens can be located in the tissue. Multilabling experiments with antibodies require availability of primary antibodies derived from different hosts and secondary antibodies specifically reacting to immunoglobulins from the hosts. Primary antibodies used Mouse anti-Nkx6.1 (1:250, Abcore #F55A10), Sheep anti-BrdU (1:500, Abcam #ab1893-125), Guinea pig anti-glucagon (1:2000, Millipore #4031-01F), Goat anti-Pdx1 (1:15000, Abcore #2027), Mouse anti-KI-67 (1:500, Pharmingen #36521A), Mouse anti-somatostatin (1:100, BioLabs #SOM-018), Rabbit anti-h-somatostatin (1:1000 Dako #A566), Rabbit anti-pancreatic polypeptide (1:100 DAKO #A619), Guinea pig-anti-insulin (1:500 Abcam #ab7842), Mouse anti-insulin (1:100 Biolaps #HUI-18). Seconday antibodies used Cy2-donkey anti-mouse (#715-225-150), Cy3-donkey anti-sheep (#713-165-147), Cy5-donkey anti-guinea pig (#706-175-148), Cy3-donkey anti-goat (#705-165-147), Cy2-donkey anti-guinea pig (#706-225-148), Cy5-donkey anti-mouse (#715-175-151), Cy2-donkey anti-rabbit (#711-225-152), Cy3-donkey anti-rabbit (#711-166-152). Nuclei were visualized by DAPI. DAPI is fluorescent stain (excited at 358 nm and fluoresce at 461 nm) that binds DNA. DAPI (stock diluted 1:1000 in 0.5% TNB blocking buffer) were applied together with the secondary antibodies. Ducts were identified by *Dolichos Biflorus* Agglutinin (DBA).

Confocal Laser Scanning Microscopy (CLSM):

Slides were scanned on a LSM 510 META Axio Imager (Zeiss). Fluorophore exitation was performed with a LSM510 laser module fitted with an Argon laser (488 nm, 50% laser power), a Helium/Neon laser (543 nm) and a Helium/Neon laser (633 nm). Plan-Neofluar 10×/0.3, 25/40×/1.3 or 63×/1.4 objectives were used. Emitted fluorescence was detected using BP 505-530 nm (Cy2), LP420 nm (DAPI) and LP 560 nm filters (Cy3). Cy5 was recorded with the LSM510 META module set to 636-754 nm. Fluorescence was recorded as square 8-bit images (1024×1024 pixels). Pixel time of 3.20 µs was used.

Processing of Tissue for Alpha/Beta Cell Mass Calculation (IHC):

The mice were killed by cervical dislocation. The gastrointestinal region was quickly removed and fixed in 10% natural buffered formalin at room temperature for 24 hours. Subsequently, the pancreas was removed, rolled to a sausage in a mesh-bag and processed to paraffin. Finally, the pancreas was cut into 4 slabs before it was embedded into a paraffin block. The blocks were cut into 3 µm sections on a microtome.

Immunohistochemistry Staining:

The sections were dewaxed in passages through xylene and ethanol to water. Antigens were retrieved by microwave heating in TEG buffer (AMPQ17020, Ampliqon) for 20 minutes, after which the slides were washed in water. Several blocking steps were applied to avoid false positive staining signal; Endogenous hydrogen peroxide was the blocked by incubating the sections for 15 minutes with 1% hydrogen peroxide followed by washing with Tris-buffered saline with 0.05% Tween-20 (TBST). Endogenous biotin was blocked by incubating the sections with avidin (X0590, DAKO) for 10 minutes followed by washing with TBST. Endogenous avidin was blocked by incubating the sections with biotin (X0590, DAKO) for 10 minutes followed by washing with TBST. Finally the sections were blocked with 0.05% TNB buffer (Perkin Elmer) for 60 minutes, which is the buffer used for the antibody cocktails. Then guinea pig-anti-insulin (1:75, A0564, DAKO), rabbit-anti-Nkx6.1 (1:2000, PA5-23070, Thermo Scientific) and mouse-anti-glucagon (1:7800, Glu-001, Novo Nordisk A/S) were diluted in 0.05% TNB buffer and applied to the sections for 60 minutes. Subsequent the sections were washed in TBST, and secondary antibodies; donkey-anti-guinea pig-Cy2 (1:100, 706-225-148, Jackson ImmunoResearch), donkey-anti-mouse-Cy5 (1:100, 715-175-151, Jackson ImmunoResearch) and donkey-anti-rabbit-biotin (1:200, 711-065152, Jackson ImmunoResearch) were mixed with a DAPI nucleic counterstain (1:1000, H3569, Invitrogen) and applied for 30 minutes. Again sections were washed in TBST and Streptavidin-HRP diluted in 0.05% TNB buffer (1:500, NEL701A001KT, Perkin Elmer) was applied for 15 minutes. Subsequent, sections were washed in TBST and TSA-Cy3 (1:100, NEL701A001KT, Perkin Elmer) was applied for 15 minutes. Finally the sections was washed with TBST and mounted in a fluorescence medium (S3023, DAKO) and cover slipped.

Image Analysis:

The stained pancreas sections were imaged in a VS120 Olympus slide scanner. Images was analysed in VIS (VisioPharm) with a threshold based algorithm. DAPI was considered positive, when signal intensity reached 1000 or above. Insulin staining was considered positive, when Cyt signal intensity reached 1500 or higher. Nkx6.1 staining was considered positive, when Cy3 signal intensity reached 1000 or higher. Glucagon staining was considered positive, when Cy5 signal intensity reached 700 or above. A beta cell was defined as a cell with nucleic Nkx6.1 expression and cytoplasmic insulin expression. An alpha cell was defined as a cell with cytoplasmic glucagon expression in the proximity of a beta cell. Alpha and beta cell areas were calculated by the software based on the manually determined thresholds and definitions. The total tissue area on the sections tissue was calculated based on the area of positive DAPI nuclei. Alpha cell mass was calculated as: alpha cell area/total tissue area, and beta cell area was calculated as: beta cell area/total tissue area. Finally, the data was normalised to the vehicle control group.

Quantitative Analysis:

All statistical analysis was performed in Prism using student's t-test and ANOVA.

Example 1: GABA Converts Alpha Cells to Beta Cells

GABA Administration:

GABA (Sigma) was administered by intraperitoneal injections of a 50-500 µM solution (per 40 g of mouse weight) prepared freshly once a week.

Results

As mentioned in WO14048788, a progressive increase in beta-like cell number is noted upon GABA administration. Lineage tracing indicate that such hyperplastic cells derive from cell having once expressed glucagon. Importantly, such neo-formed beta-like cells are functional and can repopulate islets following chemical ablation of beta-cells, the animals in question then displaying a normal life expectancy.

Example 2: Pharmacological Inhibition of Glucagon Signalling

Antibodies for Injection:

Two murine, monoclonal antibodies belonging to the class IgG1 were used for injection: For neutralization of glucagon, anti-glucagon antibody was used (GLU-001, Novo Nordisk, Bagsvaerd, Denmark). The anti-2,4,6-trinitrophenyl antibody (aTNP, Novo Nordisk, Bagsvaerd, Denmark) was used as a control. The antibodies are described in (Brand et al., 1994). The GLU-001 (5.0 mg/ml in PBS, 0.05% azide) contained 0.46 EU/mg and the aTNP (1.4 mg/ml in PBS, 0.05% azide) contained 3.9 EU/mg after endotoxin purification. Antibodies were diluted in sterile 0.9% saline (DAK) and injected into the tail vein of the mice (4 µg/g bw).

Quantitative Analysis:

All statistical analysis was performed in Excel (Microsoft). For comparing blood glucose between the two groups, I used the F-test to test for difference in variances and I used the Student's t-test for unpaired data for comparing means. P values<0.05 were considered significant. I analysed proliferation in 4 mice (3 females and 1 male) receiving the control antibody (aTNP) and 4 mice (3 females and 1 male) receiving GLU-001 for a week. The number on Pdx1, Nkx6.1 or glucagon positive cells were counted and categorized according to presence or absence of BrdU/KI-67. From each mouse more than 280 α-cells and more than 900 β-cells were examined for BrdU incorporation. Similarly, from each mouse more than 140 α-cells and more than 500 β-cells were examined for expression of KI-67. Cells were counted from distant sections (>100 µm). The percentages of cells positive for BrdU or KI-67 were calculated. I used the F-test to test for difference in variances and the Student's t-test for unpaired data for comparing means. When the F-test rejected the null hypothesis that the variances are equal, I used the unequal variance t-test (Welch's test) for comparing means. P values<0.05 were considered significant.

Results

Figure 1:
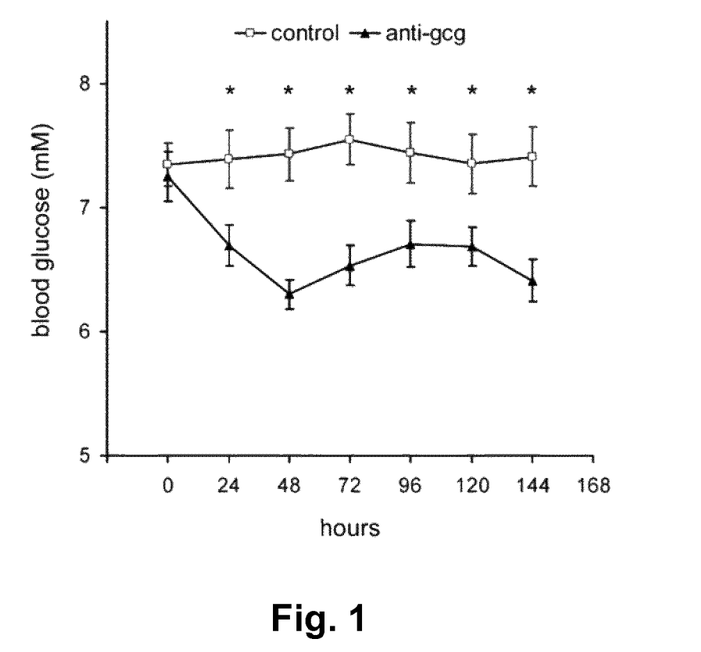
FIG. 1 shows daily injections of GLU001 (4 µg/g bw) lowers the blood glucose significantly in mice. Following daily dosing of 4 µg/g bw Glu001 or aTNP (as isotype control) a significant reduction in blood glucose was observed in mice where glucagon signalling was impaired. 9 mice were dosed with aTNP (control) and 12 mice with GLU001 (anti-gcg) injected at time=0 and every 24 h for a week.

Previous experiments in rats have applied the anti-gcg antibody GLU-001 to neutralize an exogenous glucagon load corresponding to more than 14 times the amount of glucagon released from the pancreas over a 1 h. To test if the neutralizing effect of the GLU-001 was similar in mice, 12 mice had either GLU-001 or aTNP injected and subsequently exogenous glucagon administrated. The blood glucose of mice pre-treated with the control antibody (aTNP) increased significantly in response to exogenous glucagon. The maximum of 7.4±0.1 mM was found 15 min after injection compared to an initial value of 6.8±0.2 mM.

The effect of glucagon was completely eliminated by pre-treatment with GLU-001. The mice pre-treated with GLU-001 had an initial blood glucose value of 6.7±0.3 mM compared to 6.4±0.2 mM 15 min after glucagon administration.

To determine the period of time GLU-001 can lower the blood glucose level in NMRI mice, these were injected with GLU-001 or aTNP and blood glucose was measured every 24 h. Dosing of GLU-001 significantly ($P<0.001$) lowered the blood glucose in freely feed mice 24 h after injection The blood glucose was 6.1±0.2 mM in GLU-001 treated mice compared to 6.9±0.1 mM in controls. No difference was detected 48 h after injection.

To test whether the GLU-001 was still active 24 h after injection, exogenous glucagon was injected. As expected, the blood glucose was significantly lower in GLU-001 treated mice compared to controls before injection of exogenous glucagon. However, no difference in the response to glucagon challenge was observed after 48 hours.

Immunoneutralization of Glucagon Signaling for a Week:

21 mice were injected with GLU-001 or aTNP (control) for a week. Blood samples were taken just before antibody administration. I found that the blood glucose level consistent was significantly lower for the GLU-001 treated mice compared to controls during six days. The mice had BrdU in the drinking water throughout the experiment and tamoxifen administrated orally at day 1, 3 and 5. Mouse line: Ngn3CreERTM; Rosa26R mice (6 months old). Values are mean±SE, *$P<0.05$ vs. control group (Student's t-test).

Figure 2:
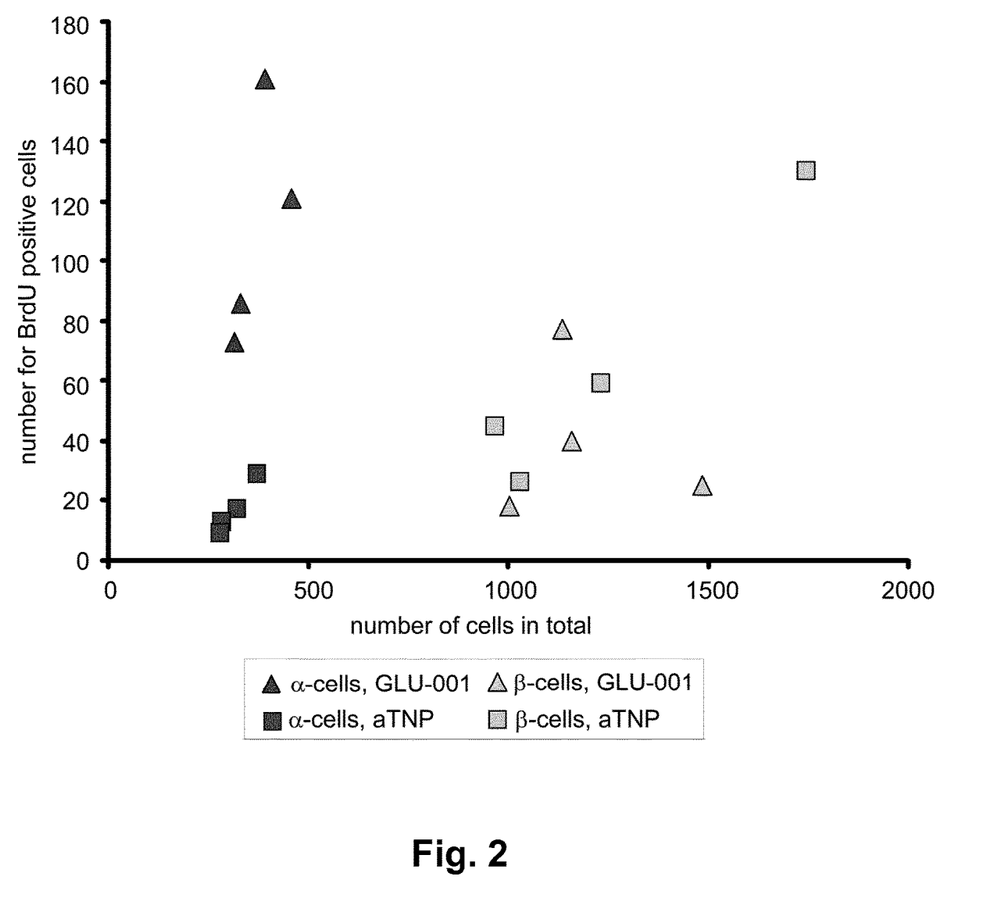
FIG. 2 shows quantitative data from the triple immunostaining for Nkx6.1, BrdU and Gcg. BrdU positive cells is plotted as a function of the total number of cells counted. Each symbol represents counting from one mouse. GLU001 treated mice had a significantly larger ratio of alpha-cells with BrdU compared to aTNP treated mice. We observed no changes in β-cells in respect to BrdU incorporation GLU001 or aTNP treated mice.

BrdU Incorporation in α-cells and β-cells:

To determine if the induced glucagon impaired glucagon signalling had induced regeneration of alpha-cells the BrdU incorporation was examined. BrdU is a synthetic nucleoside analogue of thymidine that is incorporated in newly synthesized DNA. BrdU was administrated to the mice by the drinking water throughout the experiment. Newly replicated cells were detected by an anti-BrdU antibody. BrdU stainings were performed in combination with anti-gcg and an anti-Nkx6.1 to determine the mitotic index of alpha- and beta cells respectively. In conclusion, neutralization of endogenous glucagon for a week caused a significant increase in the incorporation of BrdU in the α-cells, while β-cells were not affected.

Example 2a: Increased Glucagon Levels and Alpha Cell Mass in Response to Glucagon Inhibition Antibody for Injection:

One murine, monoclonal antibodies belonging to the class IgG1 was used for injection: For neutralization of glucagon signaling, anti-glucagon receptor antibody was used (Novo Nordisk, Bagsvaerd, Denmark). Vehicle, DPBS pH 7.4, was used as a control. The aGCGR (6.67 mg/ml in DPBS, pH 7.4) contained<0.1 EU/mg after endotoxin purification. Antibody was diluted in DPBS pH 7.4 and injected intraperitoneal into the mice (4 mg/kg body weight).

Figure 5:
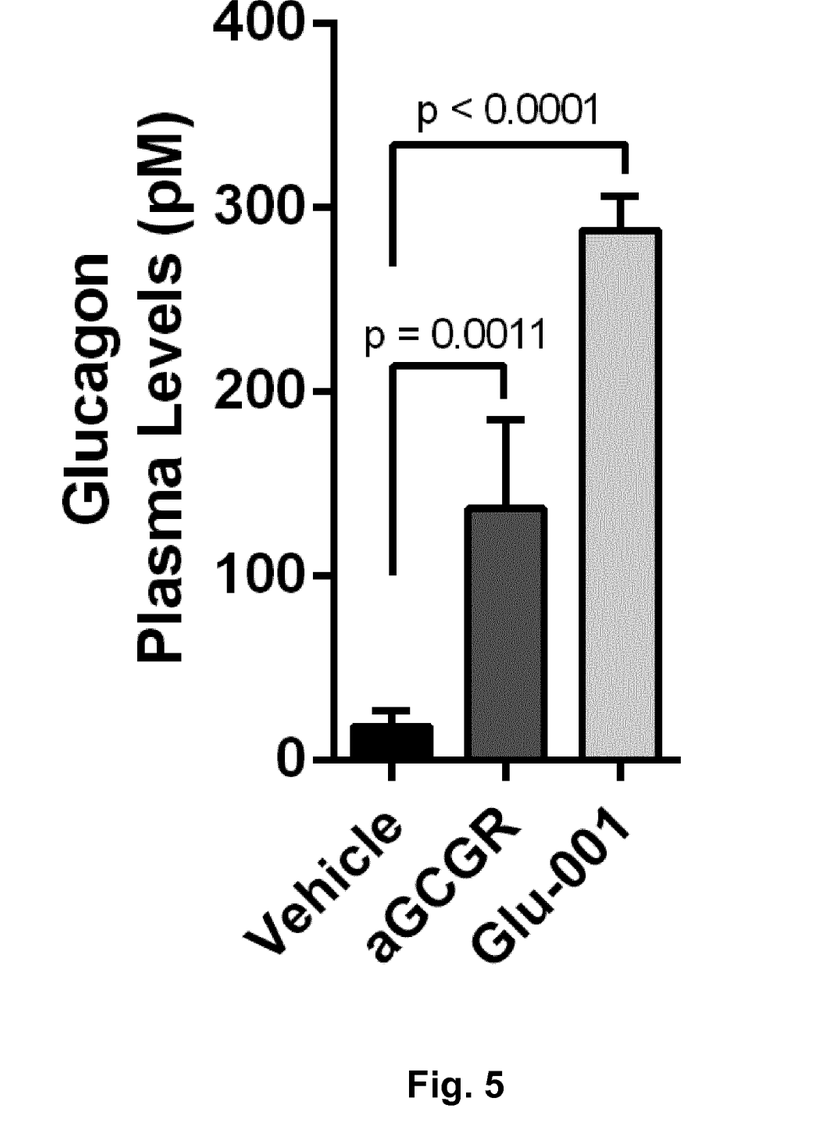
FIG. 5 shows plasma levels of circulating glucagon measured after one week of treatment with vehicle, aGCGR and GLU001. aGCGR and GLU001 treated mice had significantly increased levels of circulating glucagon compared to vehicle treated mice. Data are mean±SEM.

Results:

To test if inhibition of glucagon signalling using an anti-glucagon receptor antibody (aGCGR) would lead to increased alpha cell proliferation compared to vehicle treated mice, 10 mice were dosed 1-8 weeks with either vehicle or aGCGR. Increased circulating levels of glucagon in the plasma could serve as an indicator of increased alpha cell proliferation. Therefore, after one week of treatment, blood plasma was isolated and circulating levels of glucagon were quantified. This revealed that aGCGR treated mice exhibited significantly higher plasma glucagon levels than vehicle treated mice.

Figure 6:
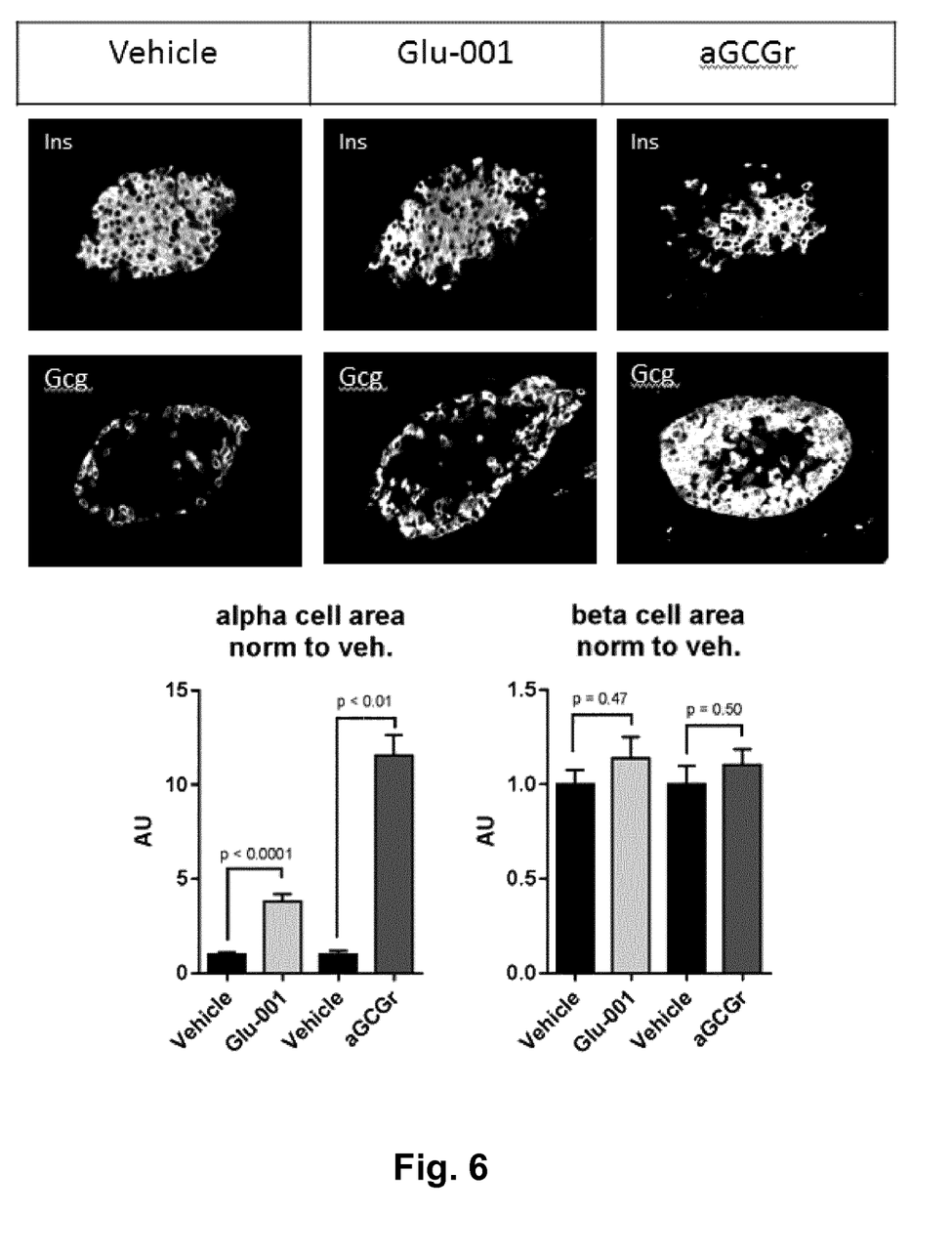
FIG. 6 shows immunohistochemistry staining with insulin and glucagon on the pancreas. The software program VIS was used to quantify alpha and beta cell area. Both Glu-001 and aGCGr treatment caused alpha cell hyperplasia and increased the alpha cell mass 3.8 fold (Glu-001) and 11.6 fold (aGCGR) compared to the vehicle treated control. The beta cell mass was unaffected by both treatments.

Alpha Cell Mass:

The pancreatic alpha cell mass was evaluated by immunohistochemistry. Pancreas was collected, fixed, processed to paraffin and 4 sections of the pancreas was stained with anti-insulin, anti-Nkx6.1 and anti-glucagon. Images of the sections was analysed in the software VIS. Beta cells were define as cell with Nkx6.1 positive nuclei and insulin positive cytoplasm. An alpha cell was defined as a cell with glucagon positive cytoplasm in a close proximity to a beta cell. Cell mass was calculated as: area of alpha cells/area of total tissue. The results showed that 1 month of aGCGR treatment induced alpha cell hyperplasia and a 11.6 fold increase in alpha cell mass compared to the vehicle control. The beta cell mass was unaffected by aGCGR treatment.

Figure 3:
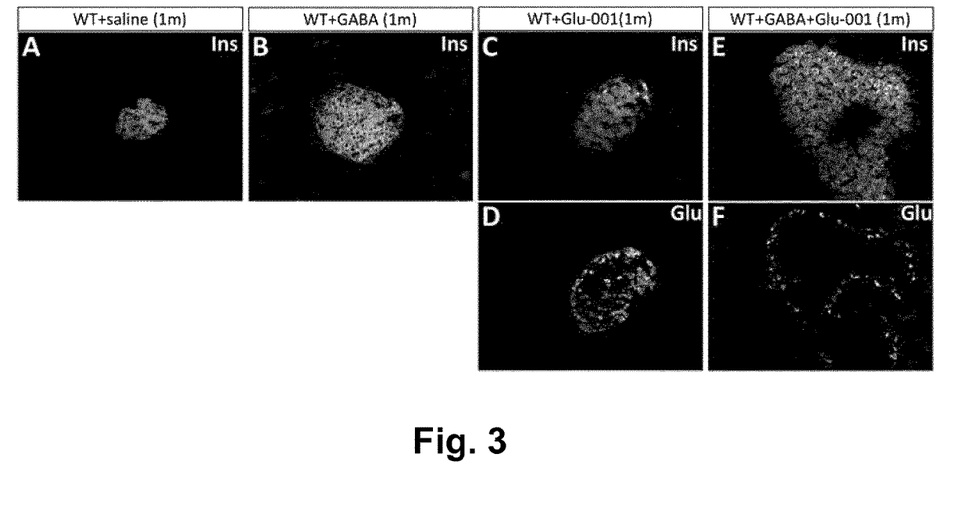
FIG. 3 shows 3-month old WT animals treated for a month with a saline solution (A), GABA (B), Glu001 (C-D) or both GABA and Glu001 (E-F). Immunohistochemical characterisation of the resulting pancreata show an increase of the insulin+cell count upon GABA treatment (B compared to A). This increase is not seen in Glu001-treated mice (C) in which we solely detected a glucagon+cell hyperplasia (D). Importantly, upon combined treatment, this glucagon+ cell hyperplasia is not seen (F) while a massive augmentation of the insulin+cell count is noted (E). This insulin+cell hyperplasia is more extensive than in "GABA only"-treated mice, demonstrating that Glu001 further increases the insulin+cell hyperplasia.

Example 3: Accelerated Regeneration of Beta-cell Mass in Mice Treated with GABA and Glu001 in Combination To determine if the combination of GABA and Glu001 could increase beta-cell mass wild type mice were treated with 1) saline, 2) GABA (daily IP injections of 50 µM/40 g mouse), 3) Glu001 (daily IP injections of 4 mg/kg) and 4) GABA+Glu001. In mice treated with saline the beta-cell mass was normal, while GABA treatment induced an expected increase in beta cell mass in expense of alpha cells. In mice treated with Glu001, the beta cell mass was comparable to that of animals treated with saline, while the alpha cell mass appeared significantly increased. However, mice treated with a combination of GABA and Glu001 displayed much bigger islets compared to all the other groups, suggesting a synergistic effect of the combined dosing. This indicates that the increase in alpha cell proliferation induced by Glu001 subsequently translates into increased beta cell mass.

Figure 4:
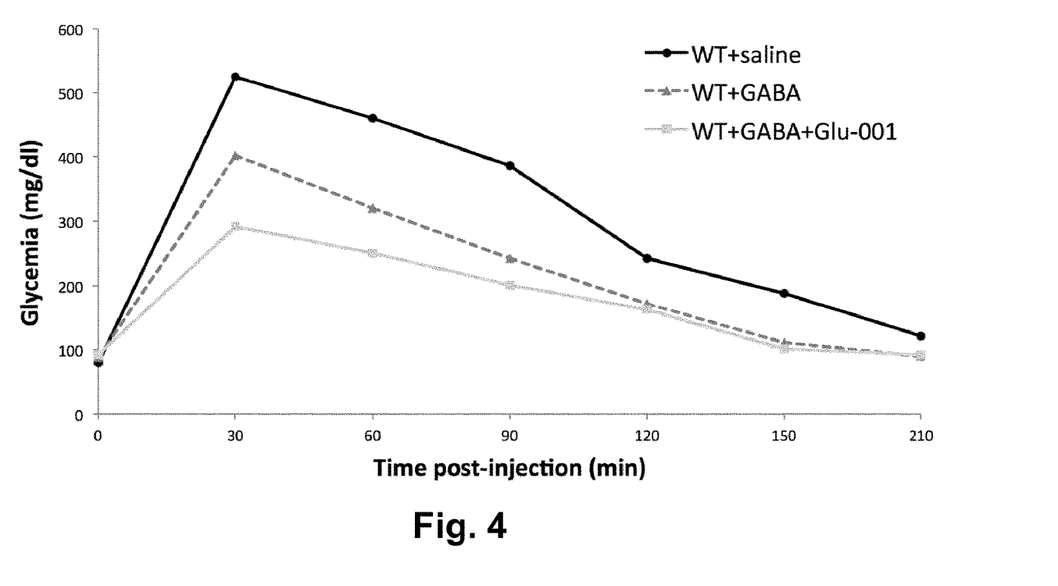
FIG. 4 shows OGTT (oral glucose tolerance test) of 3-month old WT animals treated for a month with a saline solution, GABA, or both GABA and Glu001. Note that GABA improves the response to a glucose bolus, suggestive of an increase beta-cell mass. Importantly, this response is further improved in the presence of both Glu001 and GABA, a result in line with the notion of augmented beta-like cell content.

To test if the increased beta cell mass also had an effect on glucose tolerance the mice were subjected to an OGTT. In this experiment, GABA-treated mice displayed an glucose clearance that was improved compared to untreated mice. However, the GABA Glu001 treated mice showed further improvement of the glucose clearance, suggesting that the increased beta cell mass also results in improved function.

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

REFERENCES

Al-Hasani, K., Pfeifer, A., Courtney, M., Ben-Othman, N., Gjernes, E., Vieira, A., Druelle, N., Avolio, F., Ravassard, P., Leuckx, G., et al. (2013). Adult duct-lining cells can reprogram into beta-like cells able to counter repeated cycles of toxin-induced diabetes. Dev Cell 26, 86-100.

Brand, C. L., Rolin, B., Jorgensen, P. N., Svendsen, I., Kristensen, J. S., and Hoist, J. J. (1994). Immunoneutralization of endogenous glucagon with monoclonal glucagon antibody normalizes hyperglycaemia in moderately streptozotocin-diabetic rats. Diabetologia 37, 985-993.

Furuta, M., Yano, H., Zhou, A., Rouille, Y., Hoist, J. J., Carroll, R., Ravazzola, M., Orci, L., Furuta, H., and Steiner, D. F. (1997). Defective prohormone processing and altered pancreatic islet morphology in mice lacking active SPC2. Proceedings of the National Academy of Sciences of the United States of America 94, 6646-6651.

Gelling, R. W., Du, X. Q., Dichmann, D. S., Romer, J., Huang, H., Cui, L., Obici, S., Tang, B., Hoist, J. J., Fledelius, C., et al. (2003). Lower blood glucose, hyperglucagonemia, and pancreatic alpha cell hyperplasia in glucagon receptor knockout mice. Proceedings of the National Academy of Sciences of the United States of America 100, 1438-1443.

Hayashi, Y., Yamamoto, M., Mizoguchi, H., Watanabe, C., Ito, R., Yamamoto, S., Sun, X. Y., and Murata, Y. (2009). Mice deficient for glucagon gene-derived peptides display normoglycemia and hyperplasia of islet {alpha}-cells but not of intestinal L-cells. Mol Endocrinol 23, 1990-1999.

Purwana, I., Zheng, J., Li, X., Deurloo, M., Son, D. O., Zhang, Z., Liang, C., Shen, E., Tadkase, A., Feng, Z. P., et al. (2014). GABA Promotes Human beta-Cell Proliferation and Modulates Glucose Homeostasis. Diabetes 63, 4197-4205.

Shen, D. M., Lin, S., and Parmee, E. R. (2011). A survey of small molecule glucagon receptor antagonists from recent patents (2006-2010). Expert opinion on therapeutic patents 21, 1211-1240.

Soltani, N., Qiu, H., Aleksic, M., Glinka, Y., Zhao, F., Liu, R., Li, Y., Zhang, N., Chakrabarti, R., Ng, T., et al. (2011). GABA exerts protective and regenerative effects on islet beta cells and reverses diabetes. Proceedings of the National Academy of Sciences of the United States of America 108, 11692-11697.

The invention claimed is:

1. A method for producing a population of pancreatic beta cells comprising the step of contacting a population of alpha cells with (a) GABA or a GABA receptor agonist in combination with (b) a glucagon neutralizing monoclonal antibody, selected from GLU001 or a humanized version thereof, or a glucagon receptor antagonist;

wherein said glucagon neutralizing monoclonal antibody binds glucagon and said glucagon receptor antagonist binds a glucagon receptor; and wherein glucagon receptor signaling is decreased or inhibited.

2. The method of claim 1, wherein the glucagon neutralizing monoclonal antibody binds to glucagon.

3. The method of claim 1, wherein said glucagon neutralizing monoclonal antibody is GLU001.

4. The method of claim 1, wherein glucagon neutralizing monoclonal antibody competes with GLU001 for binding to glucagon.

5. The method of claim 1, wherein glucagon neutralizing monoclonal antibody binds to same epitope as GLU001.

6. The method of claim 1, wherein the glucagon receptor antagonist is an anti-glucagon receptor antibody.

7. A pharmaceutical composition comprising (a) GABA or a GABA receptor agonist in combination with (b) a glucagon neutralizing monoclonal antibody, selected from GLU001 or a humanized version thereof, or a glucagon receptor antagonist;

wherein said glucagon neutralizing monoclonal antibody binds glucagon and said glucagon receptor antagonist binds a glucagon receptor; and wherein glucagon receptor signaling is decreased or inhibited.

8. A method of treating diabetes in a patient in need thereof comprising a step of administering to said patient an effective amount of a combination of (a) GABA or a GABA receptor agonist with (b) a glucagon neutralizing monoclonal antibody, selected from GLU001 or a humanized version thereof, or a glucagon receptor antagonist;

wherein said glucagon neutralizing monoclonal antibody binds glucagon and said glucagon receptor antagonist binds a glucagon receptor; and wherein glucagon receptor signaling is decreased or inhibited.

9. The method of claim 8, wherein the diabetes is type 1 diabetes.

10. The method of claim 8, wherein the diabetes is type 2 diabetes.

11. A method for increasing beta cells mass in a patient in need thereof comprising a step of administering to said patient an effective amount of a combination of (a) GABA or a GABA receptor agonist with (b) a glucagon neutralizing monoclonal antibody, selected from GLU001 or a humanized version thereof, or a glucagon receptor antagonist;

wherein said glucagon neutralizing monoclonal antibody binds glucagon and said glucagon receptor antagonist binds a glucagon receptor; and wherein glucagon receptor signaling is decreased or inhibited.

* * * * *